(12) United States Patent
Cunningham et al.

(10) Patent No.: US 6,399,398 B1
(45) Date of Patent: *Jun. 4, 2002

(54) ASSAY DEVICE

(75) Inventors: Carole R Cunningham, Bedford; Stewart J Wilson, Irthlingborough, both of (GB)

(73) Assignee: Unipath Limited, Hampshire (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/533,075

(22) Filed: Sep. 22, 1995

(30) Foreign Application Priority Data

Sep. 23, 1994 (GB) .............................. 9419267

(51) Int. Cl.[7] .............................. G01N 33/533
(52) U.S. Cl. .............. 436/534; 424/446; 435/7.2; 435/4; 435/287.7; 435/287.9; 435/805; 435/970; 436/510; 436/518; 436/530; 436/63; 436/65; 436/533; 436/514; 436/810; 436/814; 422/56; 422/57; 422/58
(58) Field of Search .................. 424/446; 435/7.2, 435/4, 287.7, 287.9, 805, 970; 436/510, 534, 518, 530, 63, 65, 810, 814, 533; 422/56, 57, 58

(56) References Cited

U.S. PATENT DOCUMENTS

| 4,870,005 A | | 9/1989 | Akiyoshi et al. ............... 435/7 |
| 5,122,452 A | * | 6/1992 | Yamazaki et al. ......... 435/7.92 |

(List continued on next page.)

| 5,169,757 A | * | 12/1992 | Yamazaki et al. ......... 435/7.92 |
| 5,304,467 A | | 4/1994 | Sakamoto et al. ............ 435/14 |
| 5,510,242 A | * | 4/1996 | Blais et al. ................. 435/7.32 |

FOREIGN PATENT DOCUMENTS

| EP | 0 051 183 A1 | 5/1982 | .......... G01N/33/54 |
| EP | 0 119 623 A2 | 9/1984 | .......... G01N/33/52 |
| EP | 0 204 334 A2 | 12/1986 | .......... G01N/33/52 |
| EP | 0 207 406 A2 | 1/1987 | ............. C12Q/1/48 |
| EP | 0 244 825 A1 | 11/1987 | .......... G01N/33/52 |
| EP | 0 323 605 A2 | 7/1989 | |
| GB | 2204398 | * 11/1988 | |
| WO | WO 87/03961 | 7/1987 | .......... G01N/21/78 |

OTHER PUBLICATIONS

Webster's Ninth New Collegiate Dictionary, 1985, pp. 443, 805.

Diabetes Care, vol. 14, No. 11, Nov. 1991, pp. 1094–1097.

* cited by examiner

*Primary Examiner*—Bao-Thuy L. Nguyen
(74) *Attorney, Agent, or Firm*—Morgan, Lewis & Bockius LLP

(57) ABSTRACT

An assay device comprises a sample-collecting wick made from non-woven fabric material laminated to plastics sheet. Preferably, the fabric is a 30:70 blend of viscose and polyester, and has a fibrous structure in which more than two thirds of the fibers run substantially parallel to the intended direction of liquid flow in the wick.

11 Claims, 2 Drawing Sheets

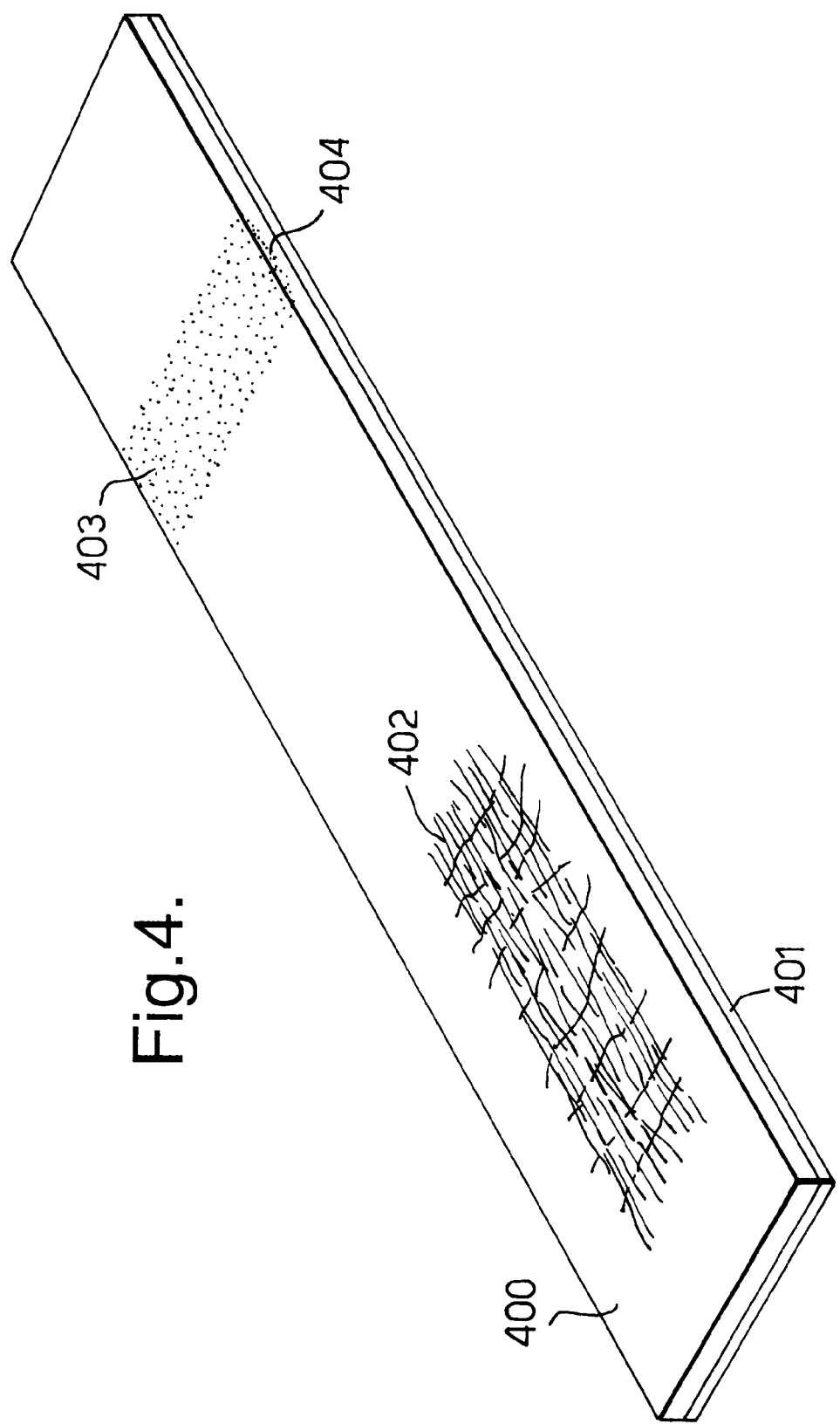

ASSAY DEVICE

FIELD OF THE INVENTION

This invention relates to assay devices.

BACKGROUND OF THE INVENTION

Many assay devices are designed to be "self-sampling" so that the user merely needs to contact the device with a liquid sample such as a body fluid in order to initiate the assay procedure. In many such devices this is the only action that the user needs to perform before the result of the assay becomes visible or readable. Many of such devices are based on the principle of "immunochromatography" in which the device contains a strip of porous carrier material along which the applied liquid sample can move. While such movement is occurring, one or more reagents within the device are carried into a detection zone on the strip and cause the assay result to be revealed. Commonly a labelled material is mobile within the strip when moist and the binding of this labelled material in the detection zone provides the means whereby the assay result becomes readable. Examples of such devices are described in EP 291 194 and EP 383 619.

The "self-sampling" facility can be provided by means of a bibulous sample receiving member or "wick". The material from which the wick is made is chosen such that applied liquid is absorbed very rapidly into the wick. The wick then acts as a reservoir of sample liquid which feeds progressively into the porous strip to drive the immunochromatographic process. The mobile labelled reagent may be incorporated in the strip itself or elsewhere within the device, upstream from the detection zone. In EP 291 194 it is suggested that the labelled reagent can be incorporated in the wick. Ideal labelled reagents useful in these assay devices are reagents (generally specific binding reagents) labelled directly or indirectly with solid water-insoluble particulate direct labels such as dye sols, metallic (eg. gold) sols, non-metallic elemental particles such as selenium and carbon, and other minute coloured particles such as coloured latex (polystyrene) particles, all known per se for this purpose.

SUMMARY OF THE INVENTION

The present invention provides an improved assay device in which the wick comprises non-woven fabric.

Preferred non-woven material is made by the process known as hydroentanglement. Ideally no chemical treatment or chemical curing is used during the manufacturing process. Such materials are already known per se and are widely used to make cleaning cloths and wipes.

For the purposes of the invention the non-woven wick material is preferably hydrophilic. If the overall character of the fabric is hydrophobic, it can be treated for example with surface active agent to render it hydrophilic in use. It will usually be made from a blend of fibres. This blend can be a mixture of hydrophobic fibres and hydrophilic fibres, but the overall character of the material preferably hydrophilic. An ideal blend comprises a mixture of viscose and polyester. Preferably, the blend is about 30% viscose and about 70% polyester.

An important preferred aspect of the invention is that the wick should comprise only a single sheet or layer of the non-woven fabric. This considerably facilitates manufacture and quality control of an assay device when the wick is used to contain one or more reagents important to the assay chemistry, such as a mobile labelled reagent. If the wick is constructed of multiple layers of bibulous material, it is difficult to ensure that the reagent(s) are deposited consistently in the wick during manufacture, and flow of sample liquid through the multi-layer structure may be uneven, and lead to inefficient or variable uptake of the reagent(s).

In order to constitute an effective wick when used in an immunochromatographic assay device, the wick should have sufficient absorptive capacity. The wick liquid capacity should exceed the capacity of the strip (together with any sink at the distal end of the strip, if provided). The "weight" of the non-woven material is important. The weight of the material is preferably at least about 50 g/m$^2$, and more preferably at least about 70 g/m$^2$. Generally it is not necessary for the weight to exceed about 120 g/m$^2$.

Preferably, the non-woven fabric layer is bonded to a supporting layer of non-water-absorbent material, such as plastics sheet. Polyester sheet is ideal. Bonding can readily be achieved using a variety of adhesives, known per se in the lamination art, the adhesion step being induced by pressure, heat or the use of two-component adhesives. It is self-evident that the quantity and nature of the adhesive should not significantly impair the absorbency and flow properties of the non-woven fabric when bonded to the support. Neither should the adhesive contain any reagents, such as unreacted excess monomers, in amounts that could interfere with the efficiency of the specific binding or other reactions that must occur within the assay device during use.

Although the fabric materials used in this invention are conventionally described as being "non-woven", this does not necessarily mean that the fibres that make up such fabric are arranged in a totally random manner. It is generally found, as a result of the process by which the fabric is made, that a distinct proportion of the fibres lie predominately in one direction and that the remainder lie predominately in a direction at right angles to the first direction. In constructing a device in accordance with the invention, the non-woven fabric is preferably selected and arranged such that the majority of the fibres lie parallel to the direction in which liquid should flow along the wick into the device. Preferably, the numerical ratio of flow-parallel fibres to flow-orthogonal fibres should be about 2:1 or greater, provided that there are sufficient flow-orthogonal fibres present to maintain the mechanical integrity of the non-woven material for manufacturing purposes.

If desired, the wick can incorporate components that assist the performance of the assay, such as buffering agents and surfactants.

Use of a wick made from non-woven fabric material of the preferred weight as described above, leads to much improved wicking properties and to very efficient release of any dried labelled reagent which may be incorporated in the wick.

BRIEF DESCRIPTION OF THE DRAWINGS

The accompanying drawings illustrate, by way of example only, an assay device constructed according to the invention:

FIG. 4 shows the detailed construction of a wick in accordance with the invention.

DETAILED DISCLOSURE OF THE INVENTION

Figure 1:
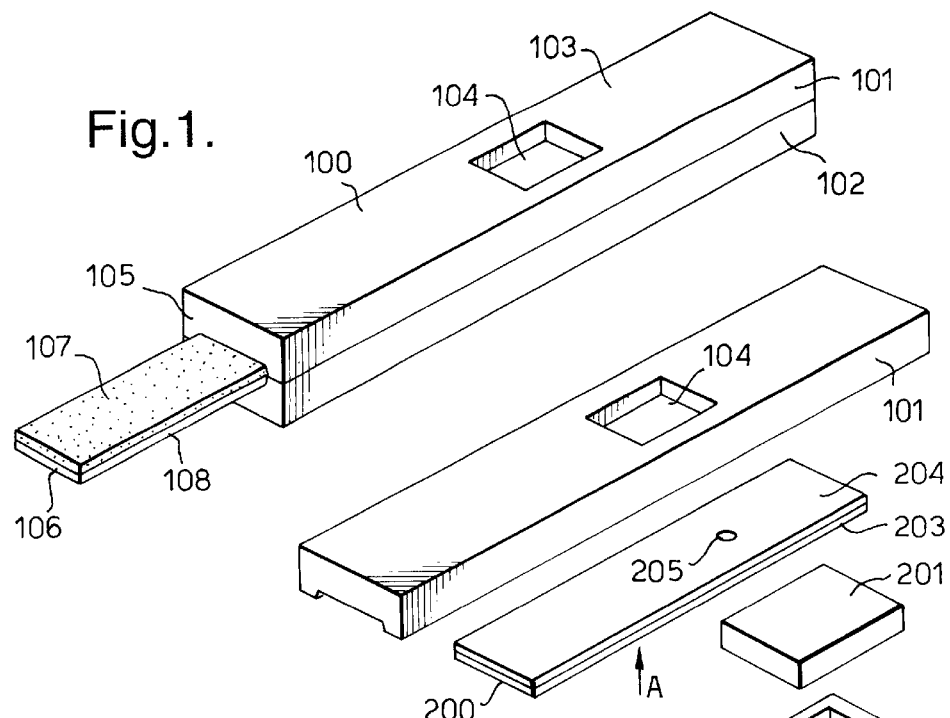
FIG. 1 shows a general view of the device exterior.

Referring to FIG. 1, the device comprises a substantially rectangular elongate casing 100 formed from upper and lower halves 101 and 102. Typically, the two halves of the casing will be moulded from plastics material or similar water-impervious material. The upper surface 103 of the casing (as seen in FIG. 1) incorporates an aperture or window 104 through which the interior of the casing can be viewed. Projecting from the left hand end 105 of the casing is a wick 106. The wick comprises an upper layer 107 of non-woven fabric material, bonded to a supporting layer 108 of plastics material such as polyester sheet.

Figure 2:
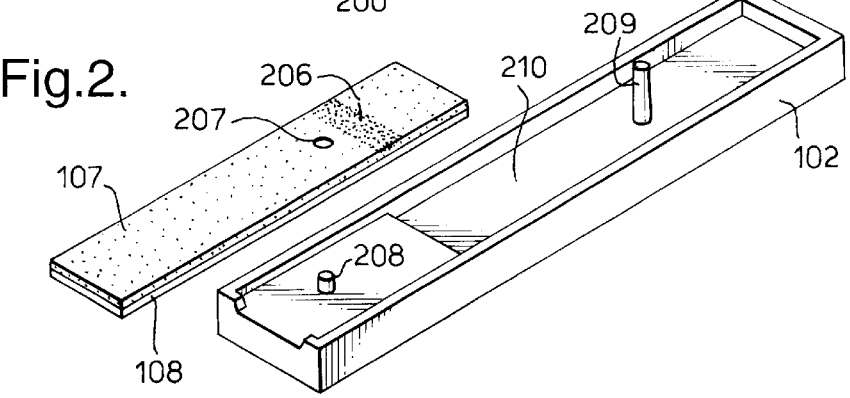
FIG. 2 shows an "exploded" view of the device of FIG. 1.

Referring to FIG. 2 which shows an exploded view of the device, the contents of the casing comprise an assay strip 200, a sink 201 and the non-exposed portion 202 of wick 106.

The assay strip 200 comprises a narrow rectangular strip 203 of porous material, such as nitrocellulose sheet, bonded to a supporting strip 204 of identical rectangular dimensions. Supporting strip 204 can be of plastics material or similar moisture-impervious material which will not affect the flow of moisture along the strip in use. The supporting strip can be transparent or translucent, so that the assay strip can be viewed through it. The assay strip can be placed against the interior of the casing adjacent aperture 104, the moisture-impervious supporting strip being used to inhibit ingress of moisture via the aperture.

The assay strip includes one or more detection zones within which the assay result is revealed by the formation or accumulation of a detectable reagent such as a coloured label which reveals the zone as a line, spot or other symbol. If desired, the assay strip can also include a control zone (generally downstream from the detection zone) to indicate to the user that the test has been performed correctly. These zones are not shown in the drawings, but will be in the region of the strip generally indicated by the letter A in FIG. 2, and therefore visible from the exterior of the casing through aperture 104. The assay strip and supporting strip are pierced by a locating hole 205.

Sink 201 can comprise any moisture-absorbent material having sponge-like properties to take up excess fluid that has progressed along the assay strip.

Wick 106 extends for a considerable distance inside the casing, and includes a region 206 towards its right hand end in which a labelled mobile component has been pre-dosed and awaits the presence of sample liquid in the wick which will render the labelled reagent mobile and transfer it elsewhere within the device. The wick is also pierced by a locating hole 207.

Lower half 102 of casing 100 acts as a tray to accomodate the various internal components. The lower half of the casing is provided with two pins or pegs 208 and 209 which extend upwards from the floor 210 of the casing. During manufacture, wick 106 is placed in the lower casing and located in a predetermined place by pin 208 passing through hole 207. The sink 201 is placed at the opposite end of the casing. The assay strip is placed over these components and located in a predetermined place by allowing pin 209 to pass through hole 205.

Figure 3:
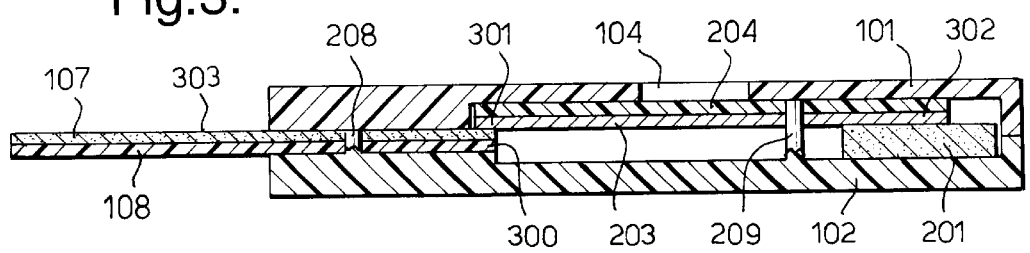
FIG. 3 shows a longitudinal cross-sectional elevation of the device of FIG. 1.

Referring to FIG. 3, which shows a cross-section of the fully assembled device, it can be seen that the assay strip 203 overlaps the right hand end 300 of the wick 107 so that liquid can flow along the length of the wick and then into the left hand end 301 of the assay strip. The right hand end 302 of the assays strip overlaps the sink 201. Therefore there is a continuous liquid flow-path from the exposed left hand portion 303 of the wick through to the sink. The upper and lower halves of the casing provide a tight seal against the wick so that moisture cannot enter the device other than by flowing through the wick material itself.

It will be appreciated that the device as illustrated in these drawings and as just described, can be modified very considerably without departing from the scope of the invention. The proportions and overall shape of the casing and other components can be altered and is largely a matter of asthetics. More than one aperture or window can be provided. The sink is an optional feature and can be discarded if the downstream portion of the assay strip has sufficient liquid capacity. It will also be appreciated that the manner in which the components within the casing are held in place is not critical to the invention, and the arrangement as shown in the drawings is provided purely by way of example.

The general construction of a wick in accordance with the invention is illustrated, by way of example, in FIG. 4 of the accompanying drawings. This figure shows a layer 400 of non-woven fabric material bonded to a supporting layer 401 of plastics sheet. The non-woven fabric has a fibrous structure 402. The wick is of rectangular form and the majority of the fibres making up the non-woven material lie substantially parallel to the long axis of the wick. Adjacent one end of the wick is a broad line 403 of deposited labelled reagent (represented by dots although the individual labelled components will not be seperately visible to the human eye). The line runs across the width of the wick. The cut edge 404 of the wick reveals that the labelled component is substantially on the surface of the wick. Deposition of the labelled reagent in this manner can readily be achieved, for example, by glazing the strip material prior to application of the labelled reagent.

EXAMPLE

The following Example demonstrates the improved properties of a wick made in accordance with the invention.

An assay device as generally described above with reference to the accompanying drawings is constructed as follows:

The device is intended to detect the presence of luteinizing hormone (LH) in urine for the purposes of an ovulation detection test. The wick is made from a commercially available non-woven fabric material consisting of a blend of viscose/polyester (30:70) having a weight of 70 gsm. The fabric is selected such that its fibrous structure is distinctly directional, with more than two thirds of the fibres running substantially parallel to one dimension. The non-woven material is infused with an aqueous Tris buffer containing by weight about 0.01% Tween 20 detergent. After drying, the non-woven material is laminated onto a polyester backing sheet of thickness about 175 $\mu$m, using a heat-sensitive adhesive. A reagent comprising anti-LH monoclonal antibodies adsorbed onto latex (polystyrene) spheres of diameter about 0.3 $\mu$m is deposited as a broad line on the non-woven material using an airbrush, as generally described in EP 291194. Subsequent mobility (under the influence of urine) of the deposited labelled reagent is enhanced by pre-treatment of the non-woven material with sucrose or other sugar to form a glaze in the region to which the latex-labelled reagent is to be applied. Alternatively, the sucrose or other sugar can be included in the deposition buffer with the labelled reagent. This is also described in greater detail in EP 291194. The line of deposited labelled reagent is orthogonal to the direction in which the fibres in the non-woven material predominantly lie.

After reagent deposition, the laminated wick is cut mechanically into strips 6 mm wide and of length about 55 mm. The long axis of the cut strip is parallel to the direction in which the majority of fibres run. The line of deposited labelled material therefore runs across the strip, and the strip is cut such that the line of deposited labelled material is adjacent one end of the strip.

Polyester-backed nitrocellulose sheet of pore size approximately $8\mu$ is converted into immunochromatographic test strips, as generally described in EP 291194, by the deposition of a line of anti-LH monoclonal antibody by a microsyringe and subsequent blocking of the nitrocellulose using polyvinyl alcohol. The treated nitrocellulose sheet is cut into test strips of width 6 mm and length about 40 mm.

The test strip and the wick are assembled within a two-part polystyrene casing in the manner described above with reference to the drawings. The casing also contains a sink comprising a pad of conventional filter paper. The test line which runs across the test strip is situated beneath the aperture in the casing.

If desired, the test strip can also incorporate a control zone (for example downstream from the detection zone) which may comprise, for example, a deposited line of anti-species antibody (such as an anti-mouse monoclonal antibody if the labelled reagent comprises a murine monoclonal).

Contact of the exposed portion of the wick with a urine sample (eg. a urine stream) causes immediate saturation of the non-woven material. The labelled reagent (protected within the casing from being washed out of the wick by contact with the external sample) is released into suspension by the absorbed urine, and the urine migrates by capillary action from the wick along the length of the nitrocellulose strip and into the sink. The labelled reagent is carried with the migrating urine. If the urine contains LH, a sandwich reaction occurs and the labelled reagent can become bound in the detection zone to reveal the presence of LH.

In a device constructed as just described, it is found that release of the deposited labelled reagent is rapid and effective and the sensitivity and reliability of the assay result is enhanced.

What is claimed is:

1. An assay device for assaying a liquid sample, said device consisting essentially of:
   a) an assay strip including one or more detection zones within which a result of said assay is revealed by an accumulation therein of a detectable reagent; and
   b) a sample receiving member to act as a reservoir of sample liquid which feeds progressively into an end of said strip, said sample receiving member incorporating said detectable reagent in a dry state and wherein said detectable reagent becomes mobile under influence of received sample liquid and is carried thereby from said sample receiving member to said one or more detection zones of said assay strip; said sample receiving member consisting essentially of a single layer of hydrophilic non-woven fabric material which has a liquid capacity exceeding the capacity of the assay strip and any sink at the distal end of the strip and which permits the sample liquid to move said reagent to the detection zone, said non-woven fabric material having a weight of at least about 50 g/m$^3$ and consisting essentially of fibres of which some lie parallel to a flow direction in which applied liquid sample must flow along said sample receiving member into said assay strip and others of said fibres lie orthogonal to said flow direction, in a numerical ratio of flow-parallel fibres to flow-orthogonal fibres of at least 2:1;

wherein, release of said dried detectable reagent is enhanced by said sample receiving member, and said assay strip and receiving member overlapping at adjacent ends thereof to further facilitate flow of sample liquid from said receiving member through said strip.

2. The device according to claim 1, in which said non-woven fabric material is a blend of viscose and polyester.

3. The device according to claim 2, in which said non-woven fabric material consists essentially of about 30% viscose and about 70% polyester.

4. The device according to claim 1, in which said non-woven fabric material has a weight of at least about 70 g/m$^2$.

5. The device according to claim 1, wherein said non-woven fabric material is bonded to a supporting layer of non-water-absorbent material.

6. The device according to claim 5, wherein said supporting layer is polyester sheet.

7. The device according to claim 1 wherein said detectable reagent is a reagent labelled with a particulate direct label.

8. The device according to claim 7, wherein said particulate direct label is coloured latex.

9. The assay device according to claim 1 wherein said sample receiving member consists essentially of a single layer or sheet of non-woven fabric material bonded to a supporting layer of non-water-absorbent material, said non-woven fabric being a blend of viscose and polyester, and said non-woven fabric having a weight of at least 50 gm/m$^2$.

10. The device according to claim 9, wherein said detectable reagent is labelled with a particulate direct label.

11. The device according to claim 10 wherein said particulate direct label is selected from the group consisting of dye sols, metallic sols, non-metallic elemental particles and coloured latex particles.

* * * * *